United States Patent [19]

Molina

[11] Patent Number: 4,534,211

[45] Date of Patent: Aug. 13, 1985

[54] TESTING APPARATUS FOR QUANTITATIVELY MEASURING CREEPABILITY OF LIQUIDS

[76] Inventor: Orlando G. Molina, 15631 Astor St., Westminster, Calif. 92683

[21] Appl. No.: 529,179

[22] Filed: Sep. 2, 1983

[51] Int. Cl.³ ............................................. G01N 13/02
[52] U.S. Cl. ................................. 73/64.4; 73/61.1 C
[58] Field of Search ......................... 73/64.4, 61.1 C; 210/658, 633, 198.3

[56] References Cited

U.S. PATENT DOCUMENTS

| | | | |
|---|---|---|---|
| 2,054,438 | 9/1936 | Natelson | 73/64.4 |
| 3,495,446 | 2/1970 | Williamson | 73/61.1 C |
| 3,513,092 | 5/1970 | Matherne, Jr. | 210/658 |
| 3,623,602 | 11/1971 | Valente | 73/61.1 C |
| 3,864,263 | 2/1975 | Jethwa et al. | 73/61.1 C |

FOREIGN PATENT DOCUMENTS

| | | | |
|---|---|---|---|
| 642962 | 9/1950 | United Kingdom | 73/64.4 |
| 693159 | 11/1979 | U.S.S.R. | 73/64.4 |

Primary Examiner—Stewart J. Levy
Assistant Examiner—Hezrow Williams

[57] ABSTRACT

A testing apparatus for quantitatively measuring the creepability property of liquids, especially tracer liquids, such as penetrants and leak tracers. The preferred embodiment of the apparatus essentially comprises: a rotatable, cylinder-like shaped base member having a longitudinal indentation therein substantially in the shape of a "V", with a depression at the vertex of the "V"; and, a metal, rectangularly-shaped panel member having a plurality of adjacent, straight, parallel-spaced grooves therein which are perpendicular to the bottom end of the panel member, with the grooves having length markings therealong indicating the distance from the bottom end, and with the panel member positioned by its bottom end in a vertical-like angled attitude in the depression of the "V"-shaped longitudinal indentation in the rotatable base member. When the liquid to be tested for creepability capability is poured into the "V"-shaped base member indentation, the liquid creeps up the grooves in the panel member. The creepability of the liquid can be quantitatively determined from the length markings (along the grooves) reached by the liquid. If necessary, the base member can be rotated rearwardly, thereby inclining the panel member rearwardly (i.e., less vertically), in order to obtain measurable readings of liquid of high viscosity.

26 Claims, 6 Drawing Figures

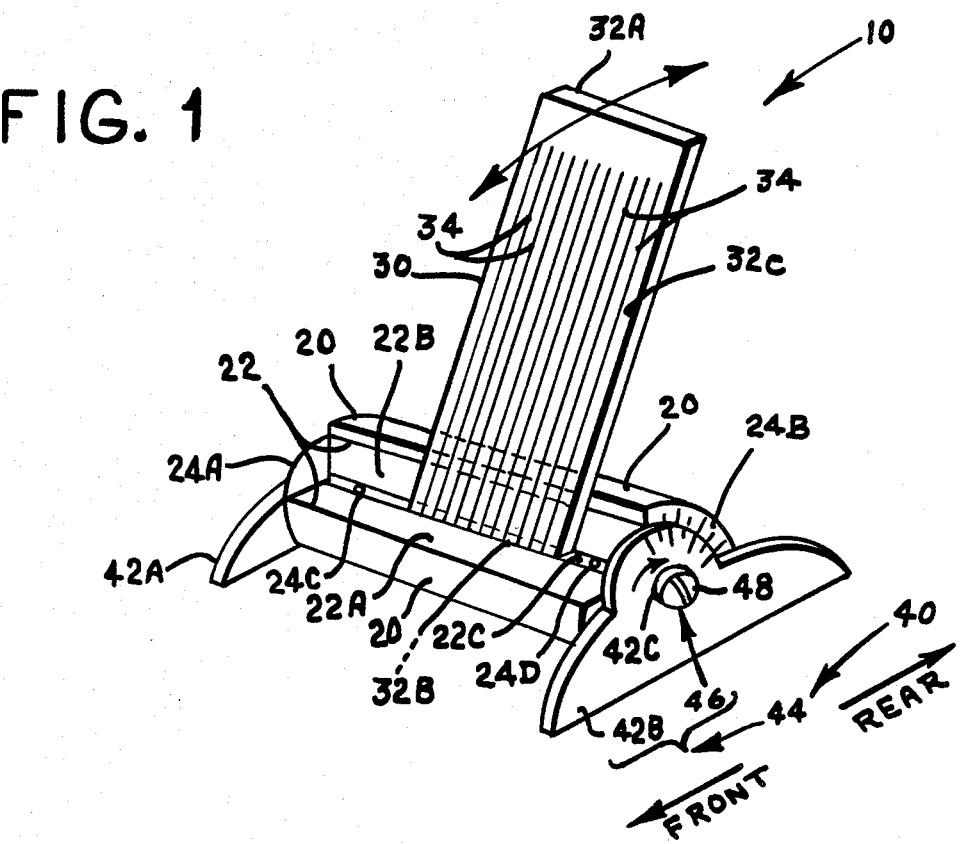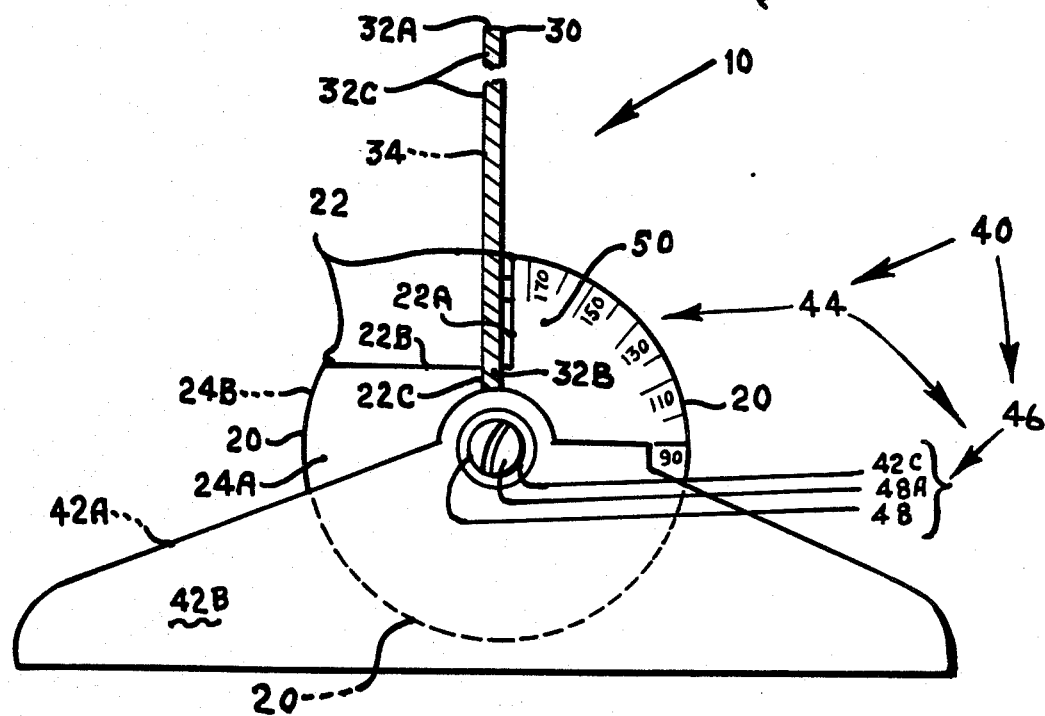

TESTING APPARATUS FOR QUANTITATIVELY MEASURING CREEPABILITY OF LIQUIDS

STATEMENT OF GOVERNMENT INTEREST

The invention described herein may be manufactured and used by or for the Government for governmental purposes without the payment of any royalty thereon.

BACKGROUND OF THE INVENTION

This invention relates generally to the testing of liquids and more particularly to a unique testing apparatus for quantitatively determining (i.e., measuring) the activity or characteristic known as creepability of liquids, especially tracer liquids, such as penetrants and fluorescent leak tracers.

The creepability (or spreadability) function of liquids containing surfactants or wetting agents which are used to lower the surface tension of penetrating-type solutions can be defined as the spontaneous mobility of a liquid as it spreads or wets the surface of a material. This function or phenomenon which is known in the penetrant inspection art as "creepability" is actually capillarity acting as it is exposed travelling on the surface of an object. Here the front of the spreading film preferentially tends to travel at a much higher speed when it encounters scratches, cracks, tight grooves, parts tightly pressed together and the like, whether they are metallic or nonmetallic.

Unfortunately, there is no means available in the prior art for quantitatively determining the aforedescribed creepability, despite the fact that there is and has been a long-felt need for such a means.

The availability of such a means would result in significant benefits to the art, such as: providing the capability of improving, or of attempting to improve, the penetration action of or creepability of penetrants and leak tracers; permitting the checking of the stability of such formulations after they have been stored or used; allowing the checking of the consistency (or quality) of a given penetrant or leak tracer solution of subsequent batches of the penetrant or leak tracer from a manufacturer's and/or from a user's standpoint; and providing the capability of selecting a penetrant or liquid solution with the highest creepability when creepability is a vitally sought characteristic, such as in a leak tracer solution.

Accordingly, what is needed in the art, and is not presently available, is the aforesaid means for quantitatively measuring creepability.

SUMMARY OF THE INVENTION

The instant invention satisfies the above-mentioned long-felt need. It, therefore, constitutes a significant advance in the state-of-the-art.

Essentially, the instant invention comprises a groove-incribed test panel member that is positioned in a vertical-like angled attitude in a depression of a "V"-like shaped longitudinal indentation of a cylinder-like shaped base member that has two ends with a drain hole near each end. In accordance with the invention, the liquid which is to be tested to quantatively measure its creepability capability is poured at the test panel member-base member interface, along the "V"-like shaped longitudinal indentation. A sufficient amount of the liquid is poured at the interface to ensure that the bottom ends of the inscribed or engraved grooves (which are preferably closely grouped, adjacent, straight, deep, and perpendicular to the bottom end of the test panel member) are all submerged in the liquid, but without the liquid being in such an excessive amount that it drains off through the drain holes near the ends of the base member. It is here to be noted that the configuration of the base member in fact allows the liquid to remain at the same level at the test panel member-base member interface without any of the liquid draining off through the drain holes. The liquid then travels (i.e., creeps) upwardly in the various grooves until the creepability of the liquid is exhausted and the liquid stops. Length markings along the grooves indicate the distance from the interface, thereby indicating how far the liquid in each groove has travelled (i.e., creeped) upwardly. The lengths travelled are averaged, and thereby the creepability properly or characteristic is quantified.

Accordingly, it is an object of the instant invention to provide a testing apparatus for quantitatively measuring (i.e., determining) the creepability (or spreading) property (i.e., characteristic, activity, function, or the like) of a liquid.

It is another object of this invention to provide the aforementioned testing apparatus, wherein said apparatus also is useable for determining the creepability property of any other liquid which has that property, such as lubricant oils, detergents, and chemicals.

It is a further object of this invention to provide the testing apparatus described hereinbefore, wherein said apparatus has an adjustable inclination angle, and wherein said apparatus is configured such as to form a self-leveling reservoir for the liquid being tested.

It is a still further object of the instant invention to provide the aforesaid testing apparatus, wherein said apparatus is structured such that it is very easy to clean after a test or between tests.

These objects of the instant invention, as well as other objects related thereto (such as simplicity, reliability, durability, ease of using, and low cost of manufacturing), will become readily apparent after a consideration of the description of the invention, together with reference to the contents of the Figures of the drawing.

DESCRIPTION OF THE DRAWING

FIG. 1 is a perspective view, in simplified pictorial and schematic form, of the preferred embodiment of the instant invention;

FIG. 2 is a side elevation view, also in simplified pictorial and schematic form, and enlarged and in detail of the preferred embodiment shown in FIG. 1;

DESCRIPTION OF THE PREFERRED EMBODIMENT AND VARIATION

Figure 3:
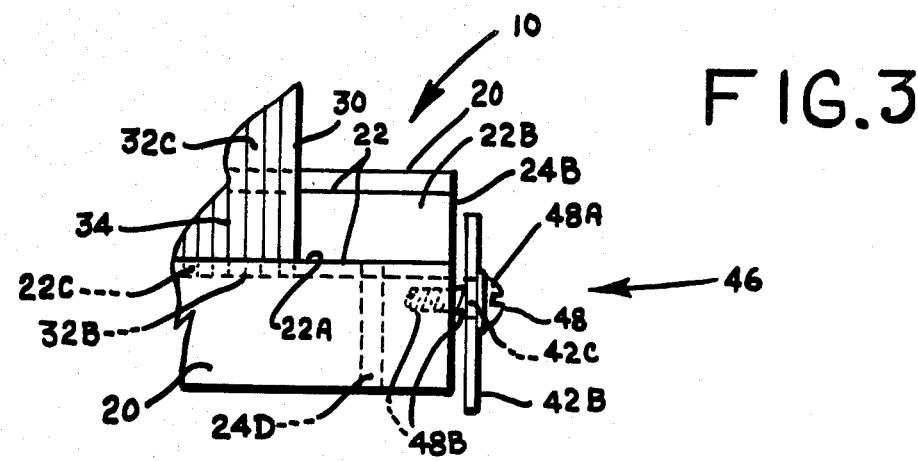
FIG. 3 is a front view, partially fragmented and in simplified pictorial and schematic form, of the preferred embodiment shown in FIGS. 1 and 2.
Figure 4:
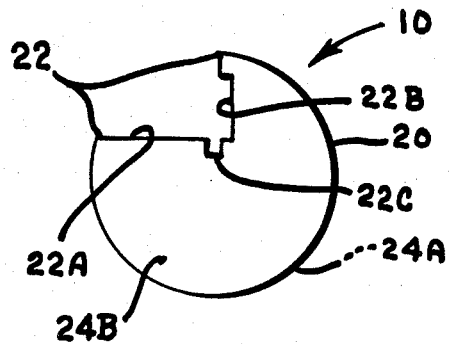
FIG. 4 is an end view of an end of the base member component of the preferred embodiment shown in FIGS. 1-3, inclusive.
Figure 5:
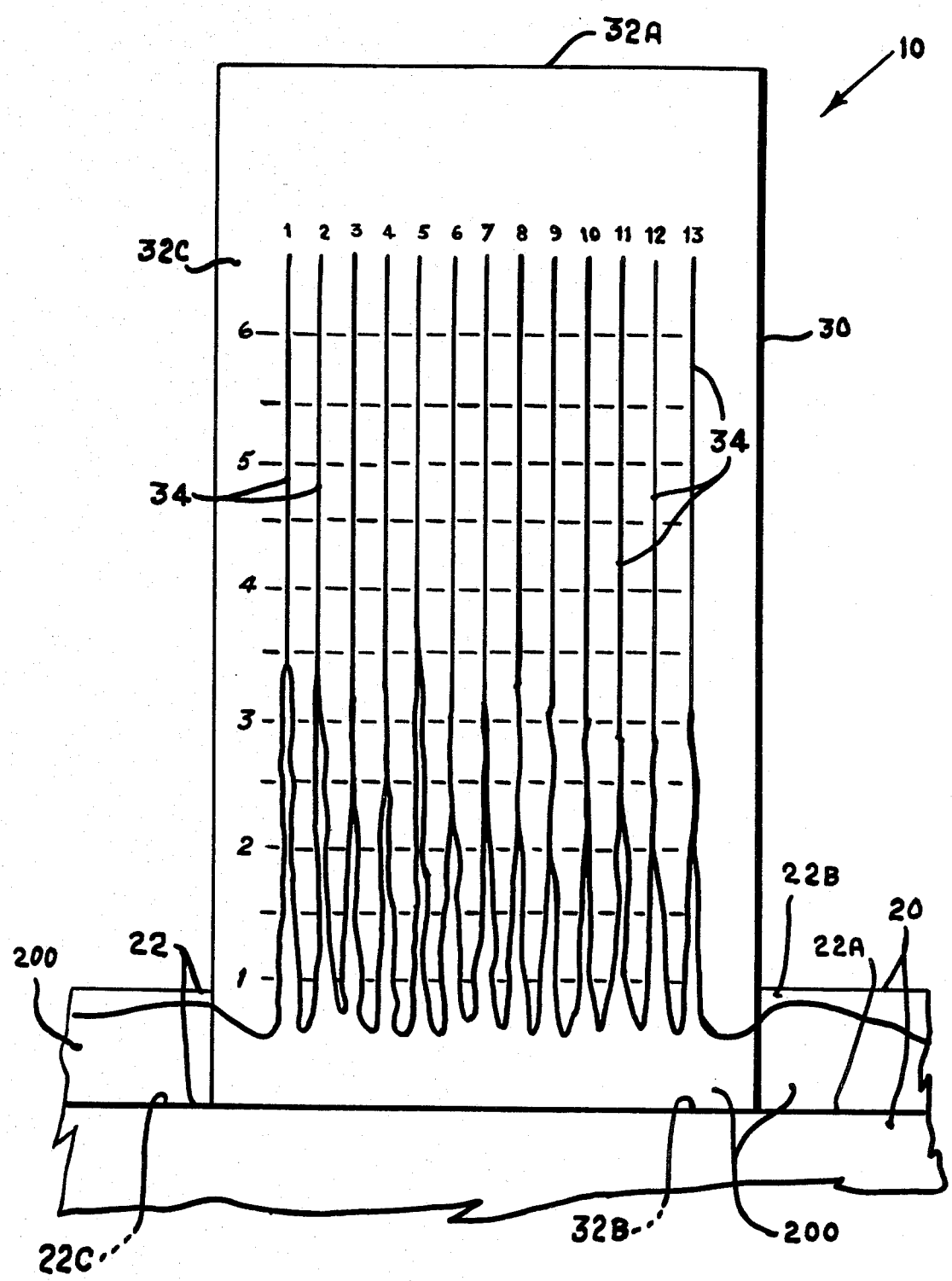
FIG. 5 is a front view, in simplified pictorial and schematic representation, partially fragmented and enlarged and in detail, of the preferred embodiment shown in FIGS. 1-4, inclusive, while in use testing a liquid for creepability.

As a preliminary matter, and with reference to FIGS. 1-6, it is to be remembered that the instant invention is for use with a liquid which has the aforementioned creepability property, such as liquid 200, FIG. 5.

In the most basic and generic structural form, the preferred embodiment 10, FIGS. 1-5, comprises: a base member 20 having a longitudinal indentation 22 therein essentially in the shape of a "V" with a depression 22C in the indentation 22 at the vertex of the "V"; a test panel member 30 made of liquid impervious material and having a top end 32A, a bottom end 32B, and a face 32C therebetween, with a plurality of adjacent straight grooves 34 positioned on the face 32C in parallel-spaced relationship to each other and running from the bottom end 32B towards the top end 32A, with markings therealong (best seen in FIG. 5) indicating the length of the grooves 34 from the bottom end 32B, and with this panel member 30 disposed face-front and with the bottom end 32B positioned in the depression 22C of the base member 20 in an essentially vertical (starting) position with the base member 20; and means (generally designated 40), operably associated with the base member 20, for selectively rotating the base member 20, and thereby inclining the panel member 30 rearwardly.

More specifically, the base member 20 has a first end 24A and a second end 24B, with a drain hole (such as 24C) in the longitudinal indentation 22 of the base member 20 near the first end 24A, and another drain hole (such as 24D) in the longitudinal indentation 22 of the base member 20 near the second end 24B. The longitudinal indentation 22 extends from the first end 24A to the second end 24B of the base member; and, said indentation 22 has constituent surfaces (such as 22A and 22B) that form the legs of the "V"-shaped indentation 22 and which are preferably, but need not be, so diverging that they are essentially perpendicular to each other. Also as a matter of preference, rather than of limitation, the base member 20 is cylinder-like in shape, with its ends 24A and 24B preferably having the shape of a sector-like portion of approximately 270 degrees of a circle, as best seen in FIG. 4.

Also more specifically, and with regard to the test panel member 30, the bottom end 32B of the panel member 30 is disposed, in the depression 22C of the longitudinal indentation 22, between the drain holes 24C and 24D. The test panel member 30 itself is sheet-like in form, and preferably is flat, with its face 32C being flat, and with its bottom end 32B being straight. Of course, in such a situation, the depression 22C in the longitudinal indentation 22 of the base member 20 is straight and complementary to the straight bottom end 32B of the flat panel member 30. When the sheet-like panel member 30 is flat it is in the geometric form of a quadrilateral, preferably in the shape of a rectangle or of a square, and the grooves 34 are perpendicular to the straight bottom end 32B of the panel member 30.

As previously stated herein, the panel member 30 is preferably made of a liquid impervious material for obvious reasons (although a liquid absorbing material, such as wood, could be used under particular circumstances in very limited situations) and, also preferably, the liquid impervious material is metal, such as aluminum, stainless steel, or copper, with aluminum being preferred in the embodiment 10 because of factors not pertinent to the invention itself. It is here to be noted that if the metal test panel member 30 is made of a metal which will corrode if the panel member 30 is used to determine the creepability of a corrosive liquid, then of course the corridible panel member 30 is coated and otherwise treated with a corrosion preventative agent, such as "Alodine 1200".

As a matter of preference, the grooves 34 that comprise the plurality of adjacent straight grooves 34 in the face 32C of the panel member 30 (and that also are preferably perpendicular to the straight bottom end 32B of the panel member 30) are closely grouped and have the same depth and width. However, it is to be noted that, without affecting the operability or reliability of the invention, each of the grooves 34 may have a different depth and a different width than any other groove 34 of the plurality thereof.

The means 40 for selectively rotating the base member 20, and thereby inclining (rearwardly) the test panel member 30, includes: a first leg member 42A connected to the base member 20 at the first end 24A of the base member 20, and a second leg member 42B connected to the base member 20 at the second end 24B of the base member 20, with the connections being such that the base member 20 is rotatable between the leg members 42A and 42B; and, means (generally designated 44), operably associated with the base member 20 and the test panel member 30, for measuring the angular inclination (e.g., in degrees, length of arc, or the like) of the test panel member 30 when the base member 20 is selectively rotated between the leg members 42A and 42B and thereby the test panel member 30 is angularly inclined (rearwardly). This angularity inclination measuring means 44 preferably includes angular degree markings on at least one end (such as second end 24B) of the two ends 24A and 24B of the base member 30, or an angular degree marked plate-like member (such as 50, FIG. 2) which is attached to that end (such as 24B) of the base member. This means 44 preferably also includes means (such as 46) for setting/adjusting the base member 20 and the angular markings thereon at a preselected angular setting. In turn, this means 46 includes a bolt member (such as 48) having a head portion 48A and a shank portion 48B, with the shank portion 48B being disposed such that the shank portion 48B passes through an opening (such as 42C) in a leg member (such as 42B) and it is embedded (as best seen in FIG. 3) in the end (such as 24B) of the base member 20 which is angularly degree marked or which has the angular degree marked plate-like member 50.

Figure 6:
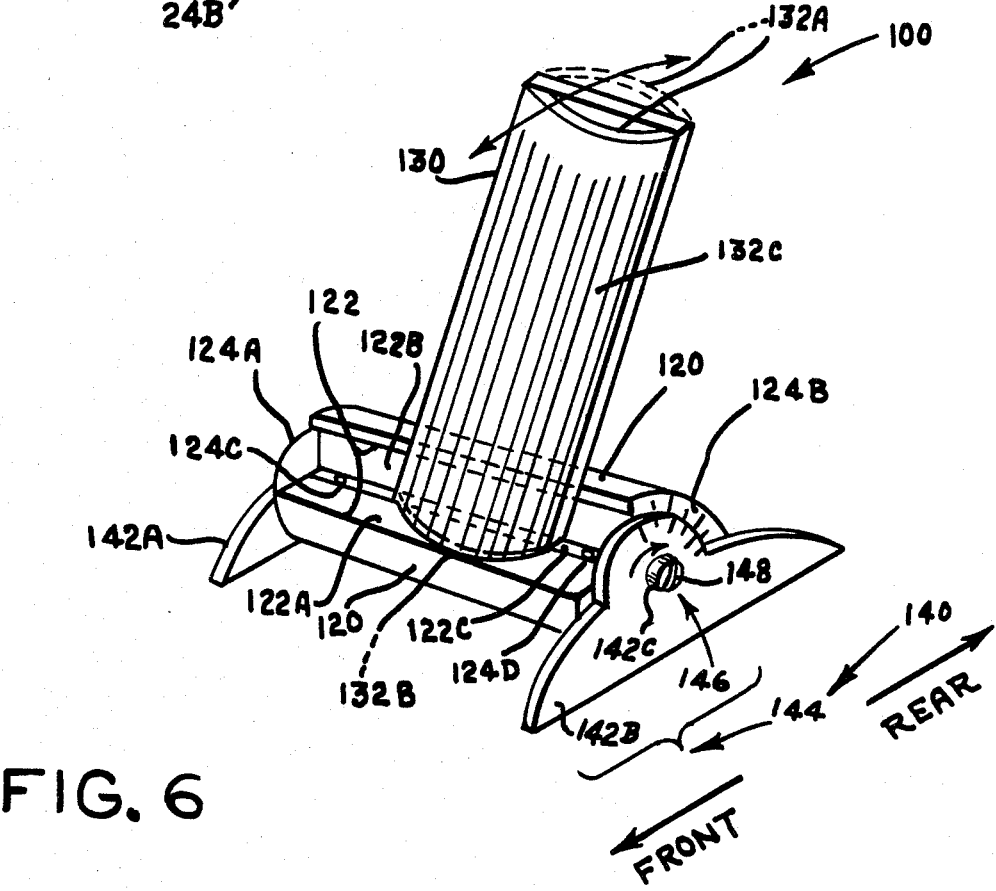
FIG. 6 is a perspective view, in simplified pictorial and schematic form, of a variation of the preferred embodiment shown in FIGS. 1-5, inclusive.

Now, with reference to FIG. 6, therein is shown in a perspective view, and in simplified pictorial and schematic form, a variation 100 of the preferred embodiment 10 shown in FIGS. 1-5, inclusive. The variation 100 is similar to the preferred embodiment 10 except that the sheet-like panel member 130 is curved, its face 132C is curved, its bottom end 132B is curved, and the depression 122C is curved and complementary to the curved bottom end 132B. The curved, sheet-like panel member 130 preferably is a portion of the cylindrical surface of a cylinder, although it can also be a portion of a nappe of a cone. As shown in FIG. 6, the curved panel member 130 can be curved outwardly (convexly, as shown) or curved inwardly (concavely, as shown in dotted lines).

MANNER OF USE OF THE PREFERRED EMBODIMENT & VARIATION

The manner of use, and of operation, of the preferred embodiment 10 (and of the variation 100 thereof) of the instant invention can be easily ascertained by any person of ordinary skill in the art from the foregoing description, coupled with reference to the contents of the Figures of the drawing.

For those not of the art, the manner of use and operation of the invention can be learned by correlating the contents of the Figures with the description of the invention, especially that portion thereof entitled "Summary of the Invention."

To all readers, it will be of interest that, in testing the instant invention, it was found that, as the liquid being tested came into contact with the panel member 30, the grooves 34 instantaneously began to serve as exposed capillarity tubes by allowing the liquid to travel upwardly. This upward effort or creepability was timed. At the end of twenty (20) seconds, the creeping activity of the liquid had been exhausted, i.e., it had come to a stop. Since the liquid used was fluorescent, black light illumination was used (white light can be used for non-fluorescent liquids), and a mark was made with a felt tip pen at the location of each groove (there were 13 in the panel member 30 used) where the upward travel had stopped. Variations in height or lengths (i.e., distance travelled) in each of these grooves was of no concern, since such variations are due to slight variations of groove depth or tightness of groove. Each height or column (i.e., distance travelled) was measured (between the markings already along the grooves) to the nearest tenth of an inch. These measurements, i.e., thirteen (13) because of the thirteen (13) grooves, were totalled and averaged. A set of three of these complete tests for one single liquid is considered sufficient, and three tests were completed with this liquid, resulting in 3 measurements of the upward travel in each of the 13 grooves, i.e., a total of 39 measurements. The entire apparatus, not only the panel member, was cleaned between (i.e., after) each test.

A comparison of these measurements (which are in inches to the nearest tenth, i.e., 1.83) between two or more liquids provides an excellent practical quantitative rating as to their relative creepability. Among other useful purposes, this information can be used to upgrade a known formulation or to select the best formulation from among the several commercially available formulations.

It is to be noted and remembered that for testing low viscosity liquids (such as a leak tracer), the position of the grooved panel member is kept almost vertical; however, as thicker and more viscous liquids are tested (such as penetrants), the grooved test panel is inclined backwardly. This allows the readings to be registered at about the middle distance of the grooves and of the panel member.

It is also to be noted and remembered that nonfluorescent liquids, such as red leak tracer and penetrants, are sprayed with a white nonaqueous developer to outline their upward travel in the grooves.

CONCLUSION

It is abundantly clear from all of the foregoing, and from the contents of the Figures of the drawing, that the stated objects of the instant invention, as well as other objects related thereto, have been achieved.

It is to be noted that, although there have been described and shown the fundamental and unique features of the instant invention as applied to a preferred embodiment 10, and a variation 100 thereof, nevertheless various other embodiments, variations, adaptations, substitutions, additions, omissions, and the like may occur to and can be made by those of ordinary skill in the art. For example, the reading of the lengths to which the tested liquid 200, FIG. 5, has creeped in the grooves 34, 134 (and the averaging of these lengths) can be automated by the use of suitable electronic scanning means coupled to a means for displaying the results and/or for printing out these results.

What is claimed is:

1. A testing apparatus for quantitatively measuring the creepability property of a liquid, comprising:
    a. a base member having a longitudinal indentation therein essentially in the shape of a "V" with a depression at the vertex of said "V";
    b. a test panel member made of liquid impervious material and having a top end, a bottom end, and a face therebetween, wherein this member has a plurality of adjacent straight grooves in said face positioned in parallel-spaced relationship to each other and running from said bottom end towards said top end with markings therealong indicating the length of said grooves from said bottom end, and wherein this member is disposed face-front and with said bottom end thereof positioned in said depression of said base member, whereby said test panel member is disposed in an essentially vertical positional relationship with reference to said base member; and
    c. means, operably associated with said base member, for selectively rotating said base member and thereby inclining said test panel member rearwardly;

whereby when a liquid is placed in said base member indentation, said liquid creeps up said grooves in said test panel member, and thereby said creepability property of said liquid can be determined from said length markings, along said grooves, reached by said liquid.

2. A testing apparatus, as set forth in claim 1, wherein said base member has a first end and a second end, with a drain hole in said longitudinal indentation of said member near said first end, and with another drain hole in said longitudinal indentation of said base member near said second end.

3. A testing apparatus, as set forth in claim 2, wherein said longitudinal indentation extends from said first end to said second end of said base member.

4. A testing apparatus, as set forth in claim 3, wherein said essentially "V"-shaped longitudinal indentation has surfaces forming the legs of said "V" and said surfaces are so diverging that they are essentially perpendicular to each other.

5. A testing apparatus, as set forth in claim 4, wherein said base member is cylinder-like in shape, with said ends thereof having the shape of a sector-like portion of approximately 270 degrees of a circle.

6. A testing apparatus, as set forth in claim 2, wherein said bottom end of said test panel member is disposed, in said depression of said longitudinal indentation of said base member, between said drain holes.

7. A testing apparatus, as set forth in claim 6, wherein said test panel member is sheet-like in form.

8. A testing apparatus, as set forth in claim 7, wherein said sheet-like test panel member is flat, said face thereof is flat, said bottom end thereof is straight, and said depression in said indentation is straight and complementary to said straight bottom end.

9. A testing apparatus, as set forth in claim 8, wherein said flat, sheet-like test panel member is in the geometric shape of a quadrilateral and said grooves are perpendicular to said straight-bottom end thereof.

10. A testing apparatus, as set forth in claim 9, wherein said quadrilateral shaped, flat, sheet-like test panel member is in the geometric shape of a rectangle and said grooves are perpendicular to said straight bottom end thereof.

11. A testing apparatus, as set forth in claim 9, wherein said quadrilateral shaped, flat, sheet-like test panel member is in the geometric shape of a square and said grooves are perpendicular to said straight bottom thereof.

12. A testing apparatus, as set forth in claim 7, wherein said sheet-like test panel member is curved, said face thereof is curved, said bottom end thereof is curved, and said depression in said indentation is curved and complementary to said curved bottom end.

13. A testing apparatus, as set forth in claim 12, wherein said curved, sheet-like, test panel member is a portion of the cylindrical surface of a cylinder.

14. A testing apparatus, as set forth in claim 12, wherein said curved, sheet-like, test panel member is a portion of a nappe of a cone.

15. A testing apparatus, as set forth in claim 1, wherein said test panel member is made of metal.

16. A testing apparatus, as set forth in claim 15, wherein said metal test panel member is made of stainless steel.

17. A testing apparatus, as set forth in claim 15, wherein said metal test panel member is made of copper.

18. A testing apparatus, as set forth in claim 15, wherein said metal test panel member is made of aluminum.

19. A testing apparatus, as set forth in claim 15, wherein said metal test panel member is made of a metal which corrodes if said member is used to measure creepability of a corrosive liquid, and wherein said corrodible member is coated and otherwise treated with a corrosion-preventive agent if said test panel member is intended for use with said corrosive liquid.

20. A testing apparatus, as set forth in claim 1, wherein said grooves in said test panel member are closely grouped.

21. A testing apparatus, as set forth in claim 1, wherein said grooves in said test panel member have different depths and different widths.

22. A testing apparatus, as set forth in claim 2, wherein said means for selectively rotating said base member and thereby inclining said test panel member includes:

a. a first leg member connected to said base member at said first end of said base member, and a second leg member connected to said base member at said second end of said base member, wherein said connections are such that said base member is rotatable between said leg members; and b. means, operably associated with said base member, for measuring the angular inclination of said test panel member when said base member is selectively rotated between said leg members and thereby said test panel member is angularly inclined.

23. A testing apparatus, as set forth in claim 22, wherein said means for measuring the angular inclination of said test panel member when said base member is selectively rotated between said leg members includes angular degree markings on at least one end of said two ends of said base member.

24. A testing apparatus, as set forth in claim 23, wherein said means for measuring the angular inclination of said test panel member further includes means for setting/adjusting the base member and the angular degree markings thereon at a preselected angular degree setting.

25. A testing apparatus, as set forth in claim 24, wherein said means for setting/adjusting the base member and the angular degree markings thereon at a preselected angular degree setting includes a bolt member having a head portion and a shank portion, wherein said shank portion is disposed such that said shank portion passes through an opening in a leg member and is embedded in said angular degree marked end of said base member.

26. A testing assembly, as set forth in claim 22, wherein said means for measuring the angular inclination of said test panel member when said base member is selectively rotated between said leg members includes a plate-like member having angular degree markings thereon which is attached to at least one end of said two ends of said base member.

* * * * *

UNITED STATES PATENT AND TRADEMARK OFFICE
CERTIFICATE OF CORRECTION

PATENT NO. : 4,534,211

DATED : August 13, 1985

INVENTOR(S) : Orlando G. Molina

It is certified that error appears in the above-identified patent and that said Letters Patent is hereby corrected as shown below:

On the title page insert
--(73) Assignee: The United States of America as represented by the Secretary of the Air Force, Washington, D.C. --.

Signed and Sealed this

Twenty-sixth Day of November 1985

[SEAL]

Attest:

DONALD J. QUIGG

Attesting Officer

Commissioner of Patents and Trademarks